United States Patent
Peng et al.

(10) Patent No.: US 6,666,963 B1
(45) Date of Patent: Dec. 23, 2003

(54) OXYGEN SENSOR

(75) Inventors: Wenfeng Peng, Mississauga (CA); P. Richard Warburton, Moon Township, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 0 days.

(21) Appl. No.: 10/217,461

(22) Filed: Aug. 14, 2002

(51) Int. Cl.[7] .................. G01N 27/26; G01N 27/404
(52) U.S. Cl. .................. 204/432; 204/412; 204/415; 204/431
(58) Field of Search .................. 204/412, 415, 204/431, 432; 205/782, 782.5, 783

(56) References Cited

U.S. PATENT DOCUMENTS 4,587,003 A * 5/1986 Tantram et al.
5,302,274 A * 4/1994 Tomantschger et al.
5,316,648 A * 5/1994 Kuhn et al.
5,344,546 A * 9/1994 Kisele et al.
5,395,507 A * 3/1995 Aston et al.
5,635,627 A * 6/1997 Bytyn \* cited by examiner

*Primary Examiner*—T. Tung
(74) *Attorney, Agent, or Firm*—Dennison, Schultz & Dougherty

(57) ABSTRACT

A compact, long-lived oxygen sensor having an aqueous electrolyte and three gas diffusion electrodes, a working electrode, a reference electrode and a counter electrode. A porous, hydrophobic means is employed in conjunction with the counter electrode to allow air pressure in the sensor to be balanced with atmospheric pressure. The working and reference electrodes are further protected from contact with flow of electrolyte from the reservoir by a separator, so that the current output is fairly independent of sensor movement.

30 Claims, 1 Drawing Sheet

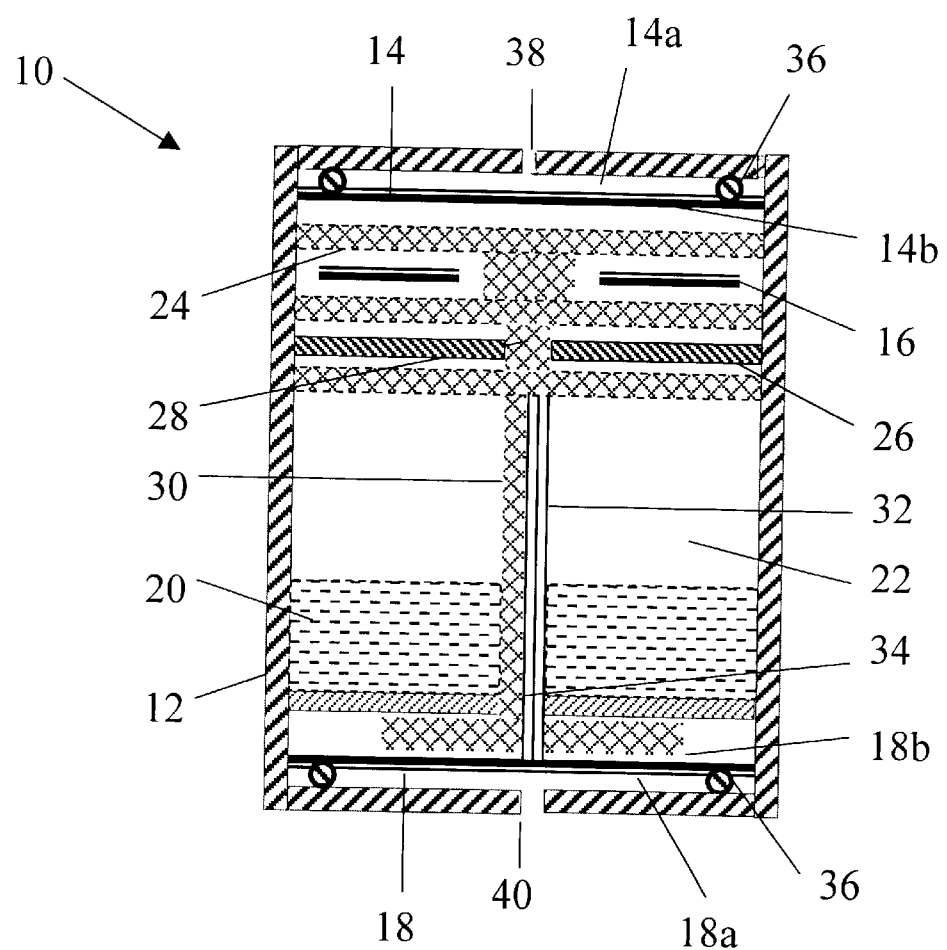
Figure

OXYGEN SENSOR

BACKGROUND OF THE INVENTION

1. Field of the Invention

The invention pertains to a three-electrode electrochemical sensor for the detection of atmospheric oxygen.

2. Description of Related Art

Most oxygen sensors in the safety market are two electrode Galvanic cells with a working electrode made of a noble metal and a counter electrode made of lead (Pb). Examples of this type of sensor are disclosed in U.S. Pat. Nos. 4,132,616 and 4,324,632. These sensors have proven to be accurate and reliable for the measurement of the oxygen ($O_2$) concentration in air; the sensors do not require long start-up times after they are installed into gas detection instruments, or after the instruments are powered back on, since the two electrodes can be "shorted", or connected with a small load resistor when not in use. However, the counter electrodes used in these sensors are consumed over time in the presence of oxygen (2 Pb+$O_2$→2 PbO), and the sensors therefore have a very limited lifetime, 1 year being typical. Furthermore, lead is a chemical hazard and an environmental toxin, and disposal of used oxygen sensors has been an increasing environmental concern.

Non-consumable oxygen sensors can be made that incorporate a noble metal/air electrode as the reference electrode. Examples of this type of sensor are described in German patent DE 4231256 C2 and U.S. Pat. No. 6,024,853. This type of sensor has three electrodes, a working electrode, a reference electrode, and a counter electrode, with an aqueous electrolyte. The potential of the working electrode is controlled by a potentiostat with respect to the potential of the reference electrode, which is typically about +1.15 V versus the standard hydrogen electrode (SHE) in an acidic medium. The potential of the working electrode is maintained sufficiently negative that reduction of oxygen proceeds rapidly on the electrode surface. The overall electrode reaction is controlled by diffusion of oxygen to electrode surface and the sensor shows a steady state current that is in direct proportion to the concentration of oxygen in air. The electrochemical reaction at the working electrode can be expressed as:

$$O_2\ (WE)+4H^++4e^-\rightarrow 2H_2O \quad (1)$$

Concurrently at the counter electrode:

$$2H_2O\rightarrow O_2\ (CE)+4H^++4e^- \quad (2)$$

The net reaction in the cell is:

$$O_2\ (WE)\rightarrow O_2(CE) \quad (3)$$

where $O_2$ (WE) and $O_2$ (CE) represent oxygen at the working electrode and at the counter electrode, respectively. Equation 3 shows that the three electrode sensor operates as an "oxygen pump", i.e. when oxygen is reduced in the sensor at the working electrode, an equal quantity of oxygen is generated in another part of sensor where the counter electrode is located. As neither the electrodes nor the electrolyte is consumed, the sensor can be operated free of maintenance for many years.

A major problem with this type of sensor has been the balancing of air pressures in and out of the sensor cell. The counter electrode is one of the key components inside the sensor, and because of constant production of oxygen gas at this electrode, a high air pressure will develop quickly inside the sensor and particularly in the electrolyte reservoir where substantial free space is normally available to allow for electrolyte expansion. If the pressure inside the sensor increases sufficiently, then liquid electrolyte will start to leak out of the cell.

U.S. Pat. No. 6,024,853 describes a sensor in which the counter electrode is located in the center of the sensor cell, and a porous PTFE disk is used in the bottom to close the cell. This sensor is very prone to leakage because the PTFE disk is covered by an electrolyte absorbent material and by free electrolyte, which can provide a gas tight seal and thereby prevent the pressure build up in the sensor from safely venting through the PTFE disk.

In another three electrode oxygen sensor that is manufactured by Draegerwek, Luebeck, Germany, the sensor has a hole in the portion of housing where the electrolyte reservoir is located, in the middle of the cell. The hole is sealed with a tube that extends inside the sensor, the tube being formed of a hydrophobic gas permeable material which allows air exchange between the inside and outside of the sensor. There are, however, several drawbacks with this design. First, the gas permeable material must have large pores to facilitate airflow, yet prevent leakage of electrolyte due to electrolyte penetration of these large pores even under low air pressure. Further, leakage of electrolyte is very likely to occur through joints of the material and the sensor housing because most gas permeable materials are made of PTFE which does not bond well to plastic surfaces.

Another major problem with oxygen sensors is motion sensitivity. Electrolyte near the counter electrode has a higher than normal concentration of dissolved oxygen, since oxygen is generated at the counter electrode. When the sensor is moved or its orientation changed, the electrolyte moves inside the electrolyte reservoir. Contact of the oxygen-rich electrolyte with either the working or reference electrode causes a significant change in electrode potential, and hence, a possible drastic change in sensor output.

In order to overcome the motion sensitivity problem, U.S. Pat. No. 6,024,853 describes a sensor in which at least one protective electrode is used. The protective electrodes are disposed around the peripheral surface of the working electrode, and are held at approximately the same potential as that of the working electrode so that the majority of dissolved oxygen can be reduced before reaching the working electrode.

The sensor, is however, much more difficult to manufacture because precise positioning of the protective electrodes is critical to achieve good performance. Since the protective electrodes must be placed close to the working electrode, electrical short-circuiting may occur. Furthermore, the sensor requires more complicated circuitry to operate than a three electrode sensor, which adds additional cost to the associated gas detection instrument.

SUMMARY OF THE INVENTION

It is therefore an object of the invention to provide a compact, long-lived oxygen sensor that is free of electrolyte leakage.

It is another object of the invention to provide a leakage-free sensor that is as accurate as a conventional, galvanic-type sensor, and that can be operated constantly in a wide range of relative humidity.

It is a further object of the invention to provide a leakage-free sensor that is a potentiostatic type, three-electrode sensor so that it is interchangeable with three-electrode toxic gas sensors in suitably designed gas detection instruments.

It is a still further object of the invention to provide an oxygen sensor that has minimal motion sensitivity, with sensor output substantially independent of changes in sensor positioning and orientation, and stable upon sensor movement.

To achieve these and other objects, the invention is directed to an electrochemical sensor for measuring atmospheric oxygen comprising:

a housing having disposed therein a working electrode, a reference electrode and a counter electrode, and an electrolyte disposed in a reservoir therefore, the reservoir including an air space over the electrolyte, each of the working electrode, reference electrode and counter electrode comprising a catalytic material disposed on a surface of a porous support;

a vent hole passing through the housing;

the counter electrode being mounted within the housing to seal the vent hole with a porous support surface facing the vent hole and a surface having catalytic material disposed thereon facing away from the vent hole; and a gas communication means connecting the counter electrode to the air space in electrolyte reservoir.

The invention is thus directed to a gas sensor in a case having, typically, a small hole at opposite ends thereof, these holes being sealed by gas permeable electrodes. Within the case is a partially filled electrolyte reservoir, having an air space therein, which also has holes at opposite ends thereof. An absorbent material passes from one end of the sensor to the other end, immobilizing the electrolyte outside of the reservoir but maintaining electrical contact with the electrodes, and a solid gas communications means contacts the counter electrode and extends into the air space in the reservoir. This arrangement permits equalization of pressure through the sensor.

Generally, the oxygen sensor of the invention is of the three electrode-type, with a working electrode, a reference electrode and a counter electrolyte, the reference electrode preferably being disposed between the working electrode and the counter electrode. All the electrodes are conventional gas diffusion type electrodes made by depositing at least one noble metal catalyst impregnated with a hydrophobic binder on a porous, hydrophobic support membrane, and is therefore gas permeable. A dilute acidic or basic aqueous solution is employed as electrolyte, which not only provides ionic conductivity between the electrodes, but also participates in electrode reactions.

The sensor of the invention includes a capillary gas access hole near the working electrode which admits gas to the sensor for detection, and which controls sensor output by limiting the flux of gas to the working electrode. Apart from this capillary hole, there is an additional gas vent opening in the sensor housing, which is made distant from the gas access hole to avoid affecting sensor operation. The counter electrode of the sensor is constructed and arranged to act as a sealing means for the gas vent opening so that electrolyte will not leak out and at the same time, oxygen generated at the electrode quickly diffuses through the gas vent opening to the outside atmosphere through the porous backing support of the counter electrode.

According to the invention, a gas communicating means is employed in conjunction with the counter electrode to balance air pressure within the cell. The gas communicating means is made of a porous, hydrophobic, chemically resistant solid material, and is disposed in such a way that it has not only significant presence in most of the empty spaces in the sensor but also has solid contact with the counter electrode.

The sensor has a large electrolyte reservoir partially charged with electrolyte. A substantial empty space is available for electrolyte expansion in the event of humidity uptake by the electrolyte under conditions of prolonged exposure to high relative humidity. A hydrophilic, chemically resistant absorbent material is packed between the electrodes to immobilize electrolyte therein. In most cases the electrolyte is able to move freely in empty spaces. According to the invention, an electrolyte separator is disposed between the reference electrode and the counter electrode, the separator having a large area so that it substantially separates the electrolyte in the working-reference electrode stack from the electrolyte in the remainder of the cell, while allowing contact of the two electrolytes through a small ionic pathway to maintain electric continuity. The electrolyte separator stops bulk flow of electrolyte in the electrolyte reservoir toward both working and reference electrodes, thus making the sensor output relatively independent of sensor movements, and changes in sensor positioning and orientation.

BRIEF DESCRIPTION OF THE DRAWINGS

The sole drawing FIGURE is a schematic cross-sectional view of an oxygen sensor according to the invention.

DESCRIPTION OF THE PREFERRED EMBODIMENTS

The FIGURE schematically shows a three-electrode oxygen sensor cell of the invention, with sensor 10 including a sensor housing 12 enclosing a working electrode 14, an adjacent reference electrode 16, and a counter electrode 18 disposed at the opposite end of the cell. An electrolyte 20 partially fills an electrolyte reservoir 22 in the central portion of the cell. The electrodes 14, 16 and 18 are in fluid contact with an electrolyte absorbent 24 which immobilizes electrolyte 20 within the sensor but outside of the reservoir. A separator 26 is disposed between the reference electrode and the reservoir so that both the working and reference electrodes are prevented from contacting free electrolyte in electrolyte reservoir 22. The separator has a small hole 28, preferably stuffed with electrolyte absorbent 24, to allow electrical continuity across the separator. The electrolyte absorbent 24 extends down to the bottom of the electrolyte reservoir 22.

Inside the electrolyte reservoir 22 is disposed an absorbent material 30 which serves as an electrolyte wicking material, and a gas communicating means 32, both of which extend through an electrolyte filling hole 34 in the bottom of the reservoir. The absorbent material 30 can be made of the same material as the electrolyte absorbent material 24, or of a similar material that is hydrophilic and chemically resistant. The absorbent wicking material physically connects the electrolyte absorbents in the working and reference electrode stack and the counter electrode 18 located in the bottom of the reservoir. The gas communicating means 32 has its top end extending into the free space in the reservoir, and its lower end in solid contact with the counter electrode 18. The hole 34 allows electrolyte to be filled into the cell before the counter electrode 18, which is then sealed by rubber O-ring 36, covers the hole.

The sensor further comprises a gas sampling hole 38, and three platinum wires (not shown) in contact with the working electrode 14, the reference electrode 16 and the counter electrode 18, respectively, for making an electrical connection between the electrodes and the external circuitry. The working electrode 14 seals the gas sampling hole 38 with an O-ring 36.

All of the electrodes are conventional gas diffusion electrodes made of at least one noble metal catalyst which can, for example, be platinum, iridium, gold, palladium, ruthenium or silver. The catalyst used can be a pure metal powder, or a metal powder supported on electrically conductive medium such as carbon, or a combination of two or more metal powders either as a blend or as an alloy. The electrodes are made by mixing the desired catalyst with a hydrophobic binder such as a PTFE emulsion on a porous, hydrophobic support membrane. Examples of suitable membranes for gas diffusion electrodes are Goretex® PTFE membranes made by W. L. Gore and Associates, Mupor® PTFE membranes by Mupor Ltd, UK, and Zitex® G-type membranes made by Norton Performance Plastics. Because of their porous, hydrophobic nature, gases easily permeate through these membranes to reach catalyst sites of the electrodes.

In the sensor shown in the FIGURE, a porous support membrane 14a of the working electrode 14 faces the gas sampling hole 38 and a catalyst layer 14b of the working electrode 14 faces away from the gas sampling hole 38. Similarly, the counter electrode 18 seals the gas vent 40 with O-ring 36, with porous support membrane 18a facing the vent, and its catalyst layer 18b facing away from the vent.

Leakage of electrolyte due to increased air pressure has been a common problem for electrochemical gas sensors employing an aqueous electrolyte, especially after being exposed to high humidity levels for an extended period of time. As noted in equation 2, water is oxidized to oxygen at the counter electrode and the air pressure gradually builds up inside the cell due to increasing partial pressure of oxygen gas. When the pressure reaches a certain critical level, the electrolyte is forced out of the cell either through the working electrode membrane, or through joints between other sensor components. In order to prevent electrolyte leakage, the counter electrode 18 according to the invention is arranged in the bottom of the sensor where a gas vent 40 is located, with the catalyst layer 18b partially covered by electrolyte absorbent which is in fluid contact with electrolyte absorbent in the working-reference electrode stack through wick 30. With the counter electrode 18 sealing the gas vent 40, quick diffusion of oxygen generated at the counter electrode to outside the cell through porous support membrane 18 and the gas vent 40 is assured.

Although liquid electrolyte on the counter electrode 18 is a barrier to the back flow of oxygen into the cell, a small amount of oxygen penetrates the electrolyte 20 and diffuses into the reservoir 22 due to the higher partial pressure on the electrode surface. The air trapped in the reservoir 22 will gradually increase in pressure and the sensor will therefore still be subject to leakage of electrolyte. According to the invention, a gas communicating means 32 is employed to release air pressure in electrolyte reservoir 22. Starting from the far point of the reservoir, the gas communicating means 32 passes through the electrolyte filling hole 34 and is firmly pressed against the counter electrode 18 at the lower end of the gas communicating means through either heat-healing or O-ring compression. As a portion of the counter electrode 18, in particular the portion in contact with gas communicating means, remains dry and gas porous, air that has moved into the gas communicating means can diffuse out of the cell through the counter electrode 18. Therefore, equilibration of air pressures is achieved without the necessity of forming a separate hole in sensor housing.

The gas communicating means 32 has low resistance to air flow, and is made of a porous, hydrophobic material such as porous PTFE. Preferably, the gas communicating means 32 has large pores and a high pore volume, e.g. internodal distances ranging from 5 to 100 $\mu$m and pore volume about 20–80%. More preferably, the material is 0.3 mm–1.0 mm thick and has 10–50 $\mu$m internodal distances and 50–70% porosity. By virtue of its hydrophobic nature, the network of pores forms reliable gas channels for gas diffusion, and these channels will not be flooded even when the material is submerged in electrolyte.

The gas communicating means 32 and the counter electrode 18 constitute a complete gas pathway, through which not only oxygen generated at the counter electrode 18 moves out of the cell, but also air pressure in the electrolyte reservoir 22 is balanced by that of the surrounding atmosphere. As the gas communicating means 32 is placed in the center of the sensor housing 12, and passes through the depth of the reservoir 22, a complete flooding of the gas communicating means 32 by electrolyte is made extremely difficult. This design allows the sensor to operate regardless of sensor orientation.

It is known that oxygen can be dissolved in the aqueous electrolyte. While the solubility of oxygen in pure water at 25° C. under 1 atmosphere is $2.5 \times 10^{-5}$ mol/L, the actual concentration of dissolved oxygen varies with the composition of the electrolyte, the temperature of the electrolyte and the atmospheric pressure. Upon applying a bias potential to the working electrode 14, oxygen (including both free oxygen in the gaseous phase and dissolved oxygen in the liquid phase on the electrode surface) is reduced to water and an oxygen depleted region develops on both sides of the electrode. When the rate by of oxygen consumption and the rate at which oxygen is replenished reach equilibrium, a steady state current is established. The contribution of oxygen diffusion from bulk electrolyte to the steady state current is very small and the main contribution comes from diffusion of oxygen from surrounding air. Nevertheless, a sudden change in the concentration of dissolved oxygen may cause a significant change in sensor output.

The noble metal/air reference electrode does not consume oxygen when the sensor is operated. However, it requires a minimal amount of oxygen to function properly. In the sensor of the invention, an appropriate oxygen concentration is maintained by back-diffusion of oxygen from the air in the electrolyte reservoir. According to the Nernst equation, the electrode potential is governed by the redox couple of oxygen/water, as is expressed by:

$$E_{ref} = E_{O2/H2O}' + 0.0148 \log [O_2] - 0.059 \text{ pH} \quad (4)$$

where $E_{O2/H2O}'$ represents the formal potential of the reference electrode, $[O_2]$ represents the concentration of dissolved oxygen, and pH represents the negative logarithm of hydrogen ion concentration of the electrolyte. Equation (4) shows that any fluctuation in the oxygen concentration will cause a change in the potential of the reference electrode and hence, a change in the potential of the working electrode via a controlling potentiostat. The resulting electrical currents that flow to re-bias the working electrode can be substantial with respect to the normal oxygen reduction current. Thus, these charging currents interfere with the accurate determination of the atmospheric oxygen concentration. Further, the change in electrode potential may be large enough that the current output is no longer limited by diffusion of gas and instead, governed by both diffusion and charge transfer kinetics on the electrode surface. This situation leads to a decreased sensor output without a change in oxygen concentration.

It is therefore necessary to protect the working and reference electrodes from exposure to electrolyte movements that may cause the oxygen concentration near the working electrode to change significantly. As mentioned above, oxygen is constantly generated at the counter electrode. Although the porous hydrophobic backing membrane of the counter electrode allows oxygen to diffuse out of the sensor cell, the partial pressure of oxygen is high and the electrolyte in immediate contact with the electrode has an increased concentration of dissolved oxygen. When the oxygen-rich electrolyte suddenly comes into contact with a large electrode area of the working-reference electrode stack, the excess oxygen quickly diffuses into the reference and working electrodes, causing a sharp change in sensor output.

In order to prevent such sudden changes in sensor output, an electrolyte separator 26 is employed according to the invention to separate electrolyte immobilized in the working-reference electrode stack from the electrolyte in the remainder of the sensor cell. The use of the separator blocks the flow of liquid electrolyte from electrolyte reservoir toward the working and reference electrodes.

The electrolyte separator is impervious to the electrolyte being used. It can be made of polymers such as polytetrafluoroethylene (PTFE), polypropylene, polyethylene, polycarbonate, polyvinylidene fluoride (PVDF) and acrylonitrile butadiene styrene (ABS). The separator is preferably at least partially hydrophobic, so that it will not be wetted quickly by the electrolyte. The separator must be large enough to effectively block the mass flow of free electrolyte and at the same time, provide an electrical pathway resulting from contact of electrolytes on both sides, a pathway which is essential to the electrical integrity necessary for the operation of the sensor. For example, most sensors have a round housing, and the separator can take the shape of a round disk with a diameter close to the inner diameter of the sensor housing. The electrolyte separator can be a porous PTFE membrane, a solid plastic disk with a small hole or secant, or the like. The hole or secant is preferably stuffed with an electrolyte adsorbent material to stop the flow of electrolyte while at the same time, maintaining electrolyte continuity across the separator.

While a smaller electrolyte pathway in the separator is desirable in providing a more stable sensor output when sensor is moving around, too small a pathway will adversely affect the sensor performance due to increased electrical resistance, in particular when the electrolyte absorbent is partly dry. A large internal resistance usually causes slow and small sensor responses, and when the pathway is very small and is filled with liquid electrolyte, diffusion of oxygen from the reservoir is restricted and a gas tight seal is formed under the working-reference electrode stack by the separator 26 and the liquid junction. As the working electrode continues to reduce oxygen, dissolved oxygen is depleted in the electrolyte surrounding the working electrode, and the reference electrode potential becomes more susceptible to changes in oxygen concentration. For example, air bubbles may break through the electrolyte separator 26 and affect the reference electrode 16 and working electrode 14 and hence, sensor output current. Thus, it is advantageous to keep the hole size in the separator 26 large enough to maintain a small oxygen diffusion flux from the counter electrode. Experimentally, an optimum electrolyte contact area between 2–10 mm$^2$ through the electrolyte separator has been found preferable.

The separator can also be made of a ceramic material such as $Al_2O_3$, silica, fritted glass or Vycor. With a low porosity and/or small pore sizes, penetration of electrolyte through the separator is very slow. The separator itself is hydrophilic, and can be wetted through by the electrolyte to maintain electrical continuity, so that neither a hole nor an electrolyte absorbent is required.

The following embodiment has been chosen to provide an illustration of the principles of the invention and its application. Other variations and modifications can be made as will be obvious to those of ordinary skill in the art.

EXAMPLE 1

Eight sensors designated as group A were built according to the embodiment disclosed in the FIGURE. Each sensor has three electrodes made from platinum black adhered to a porous PTFE membrane, and diluted sulfuric acid electrolyte. The sensor cap has a 0.125 mm i.d., 2 mm deep capillary in the center (38 in the FIGURE). A 2 mm wide, 15 mm long strip cut from a porous PTFE sheet is installed as a gas communicating means in the electrolyte reservoir. A PTFE disk membrane with a secant is used as an electrolyte separator in the bottom of the working-reference electrode stack above the electrolyte reservoir.

For comparison, 4 sensors in group B were built without gas communication means, and 4 sensors in group C were built without electrolyte separators.

All the sensors were connected to a potentiostat with a bias voltage of −400 mV (the working electrode was −400 mV more negative than the reference electrode). After about 24 hours, the sensor outputs stabilized at about 300–350 µA in clean air. However, the sensors in group B started leaking one by one in the following 7 days; the sensors in group C showed unstable outputs when moving around, and transients with a peak change of about ±0.3–0.5% $O_2$ were observed when the sensors were turned upside down. The transients lasted typically about 15–30 seconds. Sensors in group A, however, showed very stable output, with transients within ±0.05% when turned upside down. Group A sensors showed fast responses ($T_{90}$<15 s), and good linearity over the concentration range 1 to 25% oxygen, and their outputs remained unchanged for over 6 months in the tests.

What is claimed is:

1. An electrochemical sensor for measuring atmospheric oxygen comprising:

a housing having disposed therein a working electrode, a reference electrode and a counter electrode, and an electrolyte disposed in a reservoir therefore, the reservoir including an air space over the electrolyte, each of said working electrode, reference electrode and counter electrode comprising a catalytic material disposed on a surface of a porous support;

a vent hole passing through the housing;

the counter electrode being mounted within the housing to seal the vent hole with a porous support surface-facing the vent hole and a surface having catalytic material disposed thereon facing away from the vent hole;

an electrolyte separator disposed between the electrolyte reservoir and the working and reference electrodes, the separator acting as a wall of the reservoir and preventing flow of electrolyte but permitting contact of electrolyte on both sides of the separator to maintain ionic conductivity; and a gas communicating means comprising a porous, hydrophobic solid material in contact with the catalytic material surface of the counter electrode and connecting the counter electrode to the air space in electrolyte reservoir, the gas communicating means permitting venting from the cell of air pressure which builds up in the reservoir, through the counter electrode.

2. The sensor of claim 1, wherein the electrolyte separator is made of a polymer selected from the group consisting of PTFE, PVDF, polycarbonate, polyethylene, polypropylene and ABS.

3. The sensor of claim 1, wherein the electrolyte separator is made of a ceramic material selected from the group consisting of glass, silica and alumina.

4. The sensor of claim 1, wherein the separator has an opening therethrough.

5. The sensor of claim 4, wherein the opening has an area of 2–10 $mm^2$.

6. The sensor of claim 4, wherein an electrolyte absorbent material extends from the counter electrode through the electrolyte reservoir, to the working electrode and the reference electrode, passing through the opening.

7. The sensor of claim 1, wherein the gas communicating means comprises porous polytetrafluoroethylene.

8. The sensor of claim 1, wherein the gas communicating means is heat sealed to the counter electrode.

9. The sensor of claim 1, wherein contact between the gas communicating means and the counter electrode is maintained by an O-ring or gasket disposed between the counter electrode and the housing.

10. The sensor of claim 1, wherein the catalytic material comprises at least one noble metal or a mixture of at least one noble metal with an electrically conductive medium.

11. The sensor of claim 10, wherein the noble metal is selected from the group consisting of platinum, iridium, gold, palladium, ruthenium and silver.

12. The sensor of claim 10, wherein the electrically conductive medium is carbon.

13. The sensor of claim 1, additionally comprising an electrolyte absorbent material extending from the counter electrode through the electrolyte reservoir, to the working electrode and the reference electrode.

14. The sensor of claim 13, wherein the electrolyte absorbent material is selected from the group consisting of fiberglass, fritted glass, Vycor, silica powder, and a high surface area chemically impervious polymer.

15. The sensor of claim 14, wherein the polymer is selected from the group consisting of polycarbonate, polyethylene, polypropylene, PVDF and ABS.

16. An electrochemical sensor for measuring atmospheric oxygen, comprising:

a housing having a first end with a gas sampling hole therein, and a second, opposite end having a gas vent hole therein;

walls within the housing defining an electrolyte reservoir, the reservoir being partially filled with electrolyte such that an air space is defined therein, the walls defining the reservoir including a first wall comprising an electrolyte separator and an opposite second wall, at least the second wall including an opening therein;

a working electrode comprising a catalytic material disposed on a porous support, disposed within the housing at the first end thereof with the porous support disposed opposite the gas sampling hole, and with the working electrode sealing against the first end;

a reference electrode disposed within the housing between the working electrode and the first wall of the reservoir;

a counter electrode comprising a catalytic material disposed on a porous support, disposed within the housing at the second end thereof with the porous support disposed opposite the gas vent hole, and with the counter electrode sealing against the second end;

an electrolyte absorbent material extending from the air space in the reservoir to the counter electrode and passing through the opening in the second wall; and a gas communicating means comprising a porous, hydrophobic solid material extending from the air space in the reservoir to the counter electrode, the gas communicating means being in contact with the counter electrode and passing through the hole in the second wall, the gas communicating means permitting venting from the cell of air pressure which builds up in the reservoir, through the counter electrode.

17. The sensor of claim 16, wherein the electrolyte separator is made of a polymer selected from the group consisting of PTFE, PVDF, polycarbonate, polyethylene, polypropylene and ABS.

18. The sensor of claim 16, wherein the electrolyte separator is made of a ceramic material selected from the group consisting of glass, silica and alumina.

19. The sensor of claim 16, wherein the separator has an opening therethrough.

20. The sensor of claim 19, wherein the separator opening has an area of 2–10 $mm^2$.

21. The sensor of claim 20, wherein said electrolyte absorbent material also extends to the working electrode and the reference electrode, passing through the separator opening.

22. The sensor of claim 16, wherein the gas communicating means comprises porous polytetrafluoroethylene.

23. The sensor of claim 16, wherein the gas communicating means is heat sealed to the counter electrode.

24. The sensor of claim 16, wherein contact between the gas communicating means and the counter electrode is maintained by an O-ring or gasket disposed between the counter electrode and the housing.

25. The sensor of claim 16, wherein the catalytic material comprises at least one noble metal or a mixture of at least one noble metal with an electrically conductive medium.

26. The sensor of claim 25, wherein the noble metal is selected from the group consisting of platinum, iridium, gold, palladium, ruthenium and silver.

27. The sensor of claim 26, wherein the electrically conductive medium is carbon.

28. The sensor of claim 16, wherein said electrolyte absorbent material also extends to the working electrode and the reference electrode.

29. The sensor of claim 28, wherein the electrolyte absorbent material is selected from the group consisting of fiberglass, fritted glass, Vycor, silica powder, and a high surface area chemically impervious polymer.

30. The sensor of claim 29, wherein the polymer is selected from the group consisting of polycarbonate, polyethylene, polypropylene, PVDF and ABS.

* * * * *